United States Patent [19]

Koeneman

[11] 4,314,381

[45] Feb. 9, 1982

[54] HIP JOINT PROSTHESIS

[75] Inventor: James B. Koeneman, Erie, Pa.

[73] Assignee: Lord Corporation, Erie, Pa.

[21] Appl. No.: 162,845

[22] Filed: Jun. 25, 1980

[51] Int. Cl.³ .................................................. A61F 1/24
[52] U.S. Cl. ........................................ 3/1.912; 3/1.91;
128/92 C; 128/92 CA
[58] Field of Search ................................. 3/1.9–1.913;
128/92 C, 92 CA

[56] References Cited

U.S. PATENT DOCUMENTS

| | | | |
|---|---|---|---|
| 2,719,522 | 10/1955 | Hudack | 3/1.913 X |
| 3,605,123 | 9/1971 | Hahn | 3/1.9 |
| 3,707,006 | 12/1972 | Bokros et al. | 3/1.9 |
| 3,938,198 | 2/1976 | Kahn et al. | 3/1.192 |

FOREIGN PATENT DOCUMENTS 2247721  4/1974  Fed. Rep. of Germany ....... 3/1.912

Primary Examiner—Ronald L. Frinks
Attorney, Agent, or Firm—Thomas L. Kautz

[57] ABSTRACT

An improved hip joint prosthesis is provided by the present invention in which the stem portion of the femoral head prosthesis includes at least one layer of elastomeric material disposed between and attaching to at least two sections of rigid material to reduce necrosis and resorption of the adjacent bone. The stem portion may also be formed of a solid section of essentially rigid material having a plurality of circumferential elastomeric rings disposed at selected intervals along the length thereof, with at least three sections of rigid material attaching at spaced intervals to each elastomeric ring and extending outwardly to contact the bone within the medullary canal. Joint means may be provided between either of the stem portions herein and the head of the femoral head prosthesis, to provide a complete range of natural hip movement thus eliminating the need for a separate acetabulum prosthesis.

15 Claims, 7 Drawing Figures

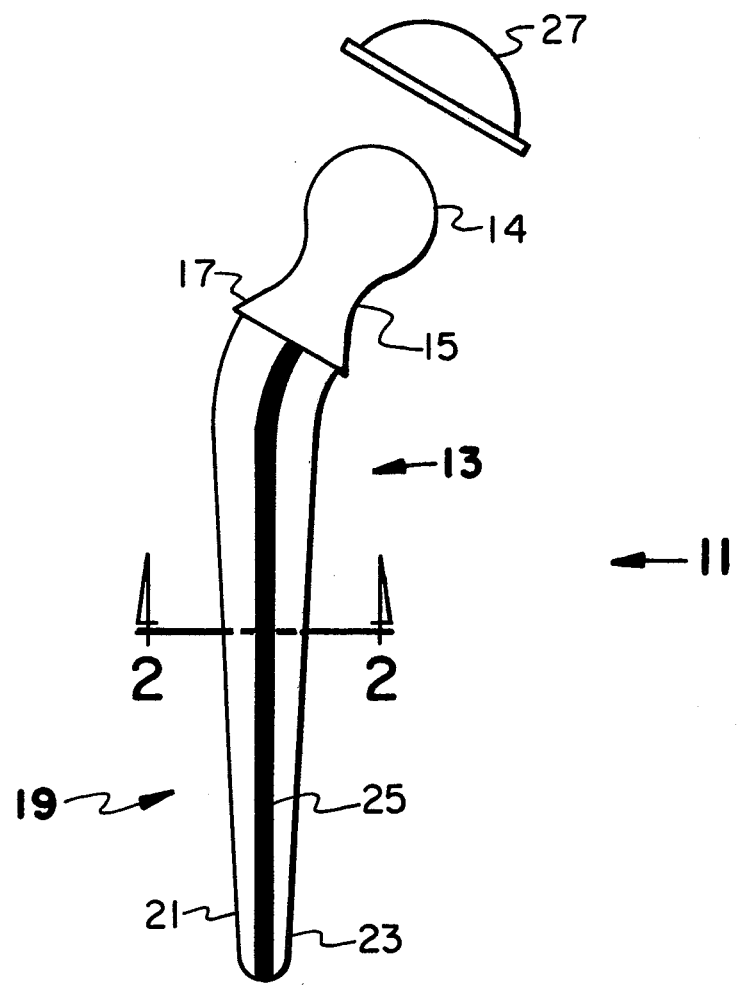
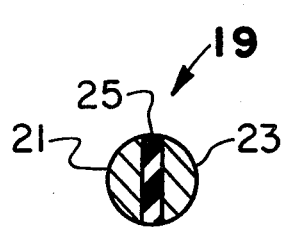 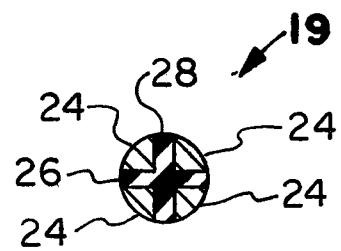
Figure 1
Figure 2     Figure 2a

HIP JOINT PROSTHESIS

FIELD OF THE INVENTION

The present invention relates generally to the field of prosthetic devices, and, more specifically, to a prosthesis for the replacement of a partial or complete coxo-femoral joint in the human body.

BACKGROUND OF THE INVENTION

Surgical techniques have been developed in recent years for the replacement of damaged or diseased joints, amputations, resections for malignancy or disease, and various types of malformation. Complete or partial replacement of the coxo-femoral or hip joint is one of the most common operations in this area, particularly among the elderly or in patients having severe arthritic conditions. Initially, hip joint surgery was limited to the repair or replacement of the femoral head, which in many of the earlier procedures was accomplished by an autologous bone graft. The major limitation of such a procedure is the necessity for opening a second surgical site to remove healthy bone for replacement into the damaged skeletal member. Moreover, the surgeon must form the healthy bone in the desired configuration in an autologous bone graft procedure within the limited time period of the operation.

Improved prosthetic devices have been developed and are now used as attachments, reinforcements or replacements to hip joints and various other skeletal members as an alternative to bone graft procedures. The primary considerations in the design of any prosthetic device is to effectively simulate the operation of a damaged body member over an extended period of time, and to achieve compatibility with the body in the damaged area. In load carrying skeletal members subjected to high stresses, such as the hip joint, compatability is achieved by not only avoiding rejection or toxic reaction of the body to the materials used in the prosthesis, but also by allowing the adjacent bone to have stresses and carry loads as if the natural hip joint was not removed.

The starting point in the design of a biocompatible coxo-femoral joint prosthesis at a recognition of the dynamics of bone growth and adaptation, and the highly controlled cellular behavior responsible for the form, size and location of bone. The cellular content of bone includes mesenchymal cells which are normally distributed on the bone surface and in miscroscopic spaces of bones. In response to loading of the bone, the mesenchymal cells become "activated" and undergo division to produce osteoclasts, or bone destroying cells. The osteoclasts undergo an internal nuclear transformation after some period has elapsed in the metabolic sequence to form osteoblasts, which are bone producing cells. Under ideal conditions, as bones in the healthy individual are subjected to normal loads and stresses, the bone destroyed by the osteoclasts equals that produced by the osteoblasts. In the event of a disruption of normal stress concentration and loading in a bone, such as what would result after a fracture, the mesenchymal cells are activated and extracellular agencies operate to selectively inhibit the activity of the osteoclasts, allowing the osteoblastic activity to dominate and replace the bone in the fractured area.

Many of the prior art hip joint prosthesis include rigid metal components having a modulus of elasticity or bending stiffness much greater than that of the femur or the acetabulum of the pelvis. Clinical studies have confirmed that such prior art prostheses often loosen after a period of years or months due to bone resorption and necrotic degeneration of the affected area, requiring a second operation in many instances. It is believed that such resorption and necrotic degeneration are caused by at least two factors. First, the localized pressure imposed on the adjacent bone by the rigid metal components tends to pinch off blood vessels and crush adjacent tissue. In addition, the relatively high resistance to bending of the rigid metal components compared to the bone in the medullary canal of the femur and in the acetabulum, creates unnatural stress concentrations in the adjacent bone. Rather than providing for natural distribution of loads and stresses on the femur and acetabulum, such prior art prostheses carry the major portion of the load imposed on the coxo-fermoral joint and adjacent bone. What the body senses is a reduction of the normal stress carrying demand on the femur and acetabulum. The mesenchymal cells are activated, but instead of the normal activity of osteoclasts and osteoblasts in a healthy bone, extracellular agencies operate to inhibit osteoblastic activity resulting in overall resorption of the bone by the osteoclasts. Thus the femur and acetabulum undergo resorption resulting in a loosening of the prosthesis after a period of time. Unfortunately, such resorption and the necrotic degeneration produced by uneven stress concentration and localized pressure may not be detected until the patient is partially rehabilitated and has begun attempts to utilize the affected skeletal member in normal activity.

The problem of localized pressure and uneven stress distribution has at least been recognized in some of the prior art patents, but a hip joint prosthesis capable of overcoming such problems was not available prior to development of the subject invention. U.S. Pat. No. 3,707,006 to Bokros et al, for example, discloses a porous ceramic substrate impregnated with a resin to obtain a joint prosthesis intended to flex and bend with the bone to avoid stress concentration at the metal-bone interface as experienced in prior art rigid metal prostheses. It is doubtful that the brittle ceramic substrate can provide a bending stiffness approximating that of bone over an extended period, and it has been found to be difficult to obtain bone and tissue ingrowth into the surface of the Bokros et al prosthesis without some type of surface treatment which tends to weaken the entire structure.

Another approach is found in U.S. Pat. No. 3,938,198 to Kahn et al, which discloses a hip joint prosthesis having a rigid solid stem covered with a layer or jacket of resilient elastomer to cushion applied loads and stresses. While some of the shock imposed on the hip and femur may be absorbed and distributed by the elastomeric layer, the Kahn et al devices does nothing to alter the bending stiffness of the stem portion which will be governed by the stiffness of the rigid metal component. In addition, the elastomer jacket of Kahn et al is covered with a fibrous overlayer formed of Dacron (polyethylene terephthalate) woven mesh, to enhance bone ingrowth. Other fibrous attachments commonly in use include polysulfone and Proplast which is a Teflon$^R$ coated graphite fiber mat. As is well known, a surface porosity of about 100 microns is needed to promote bone ingrowth, while primarily tissue ingrowth will occur with less than a 100 micron surface porosity. Recent clinical studies have shown that such low modulus fibrous attachments as mentioned above promote tissue ingrowth but not bone ingrowth, regardless of the original pore size of the material used. It is believed that the absence of bone ingrowth may be attributed to local movement of the fibrous attachments and a reduction of their pore size resulting from applied loads.

Another problem associated with existing hip joint prostheses is their inability to remain in position during the crucial rehabilitation phase where bone ingrowth takes place. This is not a concern in prostheses embedded in position with bone cement, but it has been found that problems with this technique include incomplete filing of the cavity of the bone, toxicity of the cement and possible necrosis of the adjacent layer of bone. In addition, it has been found that a prosthesis held in place by good bone ingrowth exhibits better stability and may result in better stress distribution to adjacent bone than those embedded in bone cement.

Those prior art hip joint prostheses which utilize a porous outerlayer to enhance bone ingrowth, are typically held in place by pins attached to the femur and pelvis adjacent the interface between the femur and acetabulum. The Kahn et al patent is one example. Although the problem of prosthesis stability during the early stages of bone ingrowth may not be serious in skeletal members which can easily be placed in a cast or otherwise restricted from movement, it is very difficult to avoid movement of the hip joint unless the patient is totally immobilized. Some movement of the affected hip is virtually unavoidable. Merely pinning the hip prosthesis at the femur-actebulum interface does not prevent movement of the stem portion of the prosthesis within the femoral medullary canal. Moreover, the location and implantation of such pins adds another step to the operating procedure which can be avoided as discussed below.

SUMMARY OF THE INVENTION

The present invention provides a femoral head prosthesis and a separate acetabulum prosthesis for complete or partial replacement of the coxo-femoral joint which substantially elminates necrotic degeneration and bone resorption. The stem portion of the femoral head prosthesis herein, formed of a porous titanium or a suitable equivalent for insertion into the medullary canal of the femur, is split in at least two sections with layers of biocompatible elastomer attached therebetween in a sandwich-type configuration. The stem has sufficient strength to accommodate the forces and moments created by loads imposed on the hip joint, but also exhibits minimal bending stiffness to enable adjacent sections of the femur to assume loads and stresses of the magnitude encountered in a natural hip joint. In addition, the stem section may have a diameter slightly larger than that of the medullary canal of the femur, such that upon insertion of the stem the elastomer layer or layers are compressed and urge the titanium sections into contact with the adjacent bone. This not only enhances tissue ingrowth into the porous titanium, but resists dislocation of the femoral head prosthesis along its entire length which could result from movement of the patient during the early stages of rehabilitation.

In another embodiment of the subject invention, a ball-and-socket joint means is provided in which a section of resilient elastomer is disposed between and attaches to the femoral head and a spherical-shaped pivot component formed as part of the stem, to permit rotation of the femoral head relative to the stem about three axes. The femoral head is formed for permanent insertion into the acetabulum and may be secured by bone cement or through bone ingrowth. This embodiment of the present invention eliminates a separate acetabulum prosthesis.

Accordingly, it is an object of the present invention to provide a joint prosthesis for partial or complete replacement of the coxo-femoral joint.

It is another object of the subject invention to provide a prosthesis having a stem portion formed in at least two spaced apart outer rigid sections between which at least one layer of resilient elastomer is attached, such that the resilient elastomer has at least a portion of its volume located as an innermost core part of the stem.

It is a further object of the subject invention to provide a prosthesis having a stem portion formed in at least two sections between which a layer of resilient elastomer is attached and compressed upon insertion of the stem into the femoral cavity, such that the separate sections are urged outwardly into engagement with the adjacent bone of the femur.

It is a still further object of the present invention to provide a hip joint prosthesis in which the femoral head is formed for direct insertion into the acetabulum and is fixed therewithin, the movement of the hip joint being accommodated by a resilient body of elastomer disposed between and attaching to the femoral head and pivot component formed at one end of the stem.

DESCRIPTION OF THE DRAWINGS

Objects in addition for the foregoing will become apparent upon consideration of the following description, taken in conjunction with the drawings, wherein:

FIG. 1 is a perspective view of one embodiment of the present invention in which the stem portion is split into at least two sections with an elastomeric layer(s) attached therebetween.

FIG. 2 is a cross-sectional view of the stem portion of the prosthesis herein taken generally along the line 2—2 of FIG. 1.

FIG. 2-A is a cross-sectional view taken generally along line 2—2 of FIG. 1, showing an alternate embodiment of the stem portion of the present invention.

DETAILED DESCRIPTION OF THE INVENTION

Figure 3:
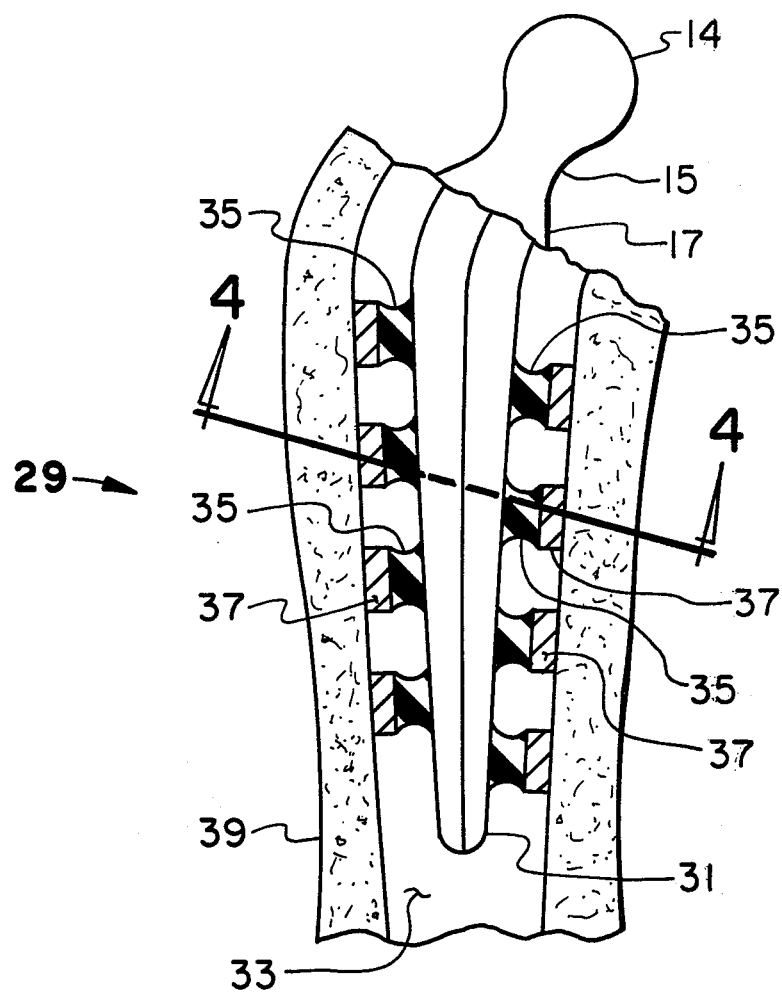
FIG. 3 is a partial cross-sectional view of a second embodiment of the present invention showing the prosthesis in place within the femur.

Referring now to the drawings, and in particular to FIG. 1, the hip joint prosthesis of the present invention is labelled generally with the reference 11. The prosthesis 11 includes a femoral head prosthesis 13 having a spherical femur head 14 tapering to a neck portion 15 which flares outwardly to form a flange section 17. In the embodiment of the present invention shown in FIG. 2, a stem 19 attaching to flange 17 is formed in the general shape of the medullary canal of the femur and split into two sections 21 and 23 respectively. A layer of biocompatible elastomer 25 is disposed between and attaches to sections 21 and 23 in a sandwich-like configuration. Alternatively, stem 19 may be split into four sections, each labelled with the reference 24 in FIG. 2A, with two layers of biocompatible elastomer 26 and 28 oriented at a right angle to one another disposed therebetween. In both of the embodiments shown in FIGS. 2 and 2A, a hemispherical acetabulum prosthesis 27 is also provided which is fixed to the acetabulum of the pelvis to receive the femur head 14 of prosthesis 11. The acetabulum prosthesis 27 is preferably formed of a physiologically inert polymer material such as polyethylene to provide a hard, relatively smooth bearing surface for the femur head 14.

As mentioned above, bone resorption and prosthetic instability during the initial bone ingrowth stage of postoperative rehabilitation are two problems encountered in the use of prior art hip joint prosthesis. Rigid metal stem sections found in many existing prostheses are believed to cause bone resorption and necrosis by carrying most of the loads imposed on the affected area, as discussed above. The present invention solves this problem by splitting the stem 19 into either two or four sections, and attaching one or more layers of elastomer therebetween. Tests have confirmed that such sandwich-like configurations of stem 19 (FIG. 2 or 2A) reduce its bending stiffness to a point where the femur and acetabulum are subjected to stresses of a magnitude approaching that encountered with natural hip joints, thus minimizing resorption and necrosis. The two-section configuration of FIG. 2, with the single layer of elastomer 25 disposed between sections 21 and 23, accommmodates the lateral-medial moments imposed on the prosthesis 11. The four-section alternative configuration of prosthesis 11 shown in FIG. 2A, in which stem 19 is divided into four sections 24 with an additional layer of elastomer 26 disposed therebetween at a right angle to elastomer layer 28 (which corresponds to elastomer layer 25 in FIG. 2), accommodates the lesser anterior-posterior moments as well as the lateral-medial moments imposed on the prosthesis 11. Prosthesis 11 may be formed of cobalt-chrome, stainless steel or titanium-based alloys, all of which exhibit sufficient strength to avoid failure and are bicompatible. In addition, the stem sections 21, 23 and 24 are preferably treated in a known manner to obtain a surface porosity of at least 45 microns to accept bone and tissue ingrowth from the adjacent bone of the femur.

The problem of prosthetic instability during the early stages of bone ingrowth is a particularly difficult one in the case of the hip joint. Some movement of the patient, with attendant stresses imposed on the hip, are virtually impossible to avoid. Pinning the flange portion 17 of the prosthesis 11 to the cortical bone of the femur does not effectively prevent movement of stem 19 within the medullary canal of the femur where bone and tissue ingrowth is critical. This problem is avoided herein by forming the stem 19 of a diameter slightly greater than the medullary canal of the femur after it is reamed out during the surgical procedure. When inserted into the medullary canal, the elastomer 25 of stem 19 is compressed and urges sections 21 and 23 outwardly into engagement with the adjacent bone providing enhanced stability along the entire length of stem 19. This is also true for the embodiment of FIG. 2A. Thus, during the critical bone ingrowth period of postoperative rehabilitation, the stem 19 is held relatively firmly in place along its entire length within the medullary canal and resists displacement which could result from movement of the patient.

Figure 4:
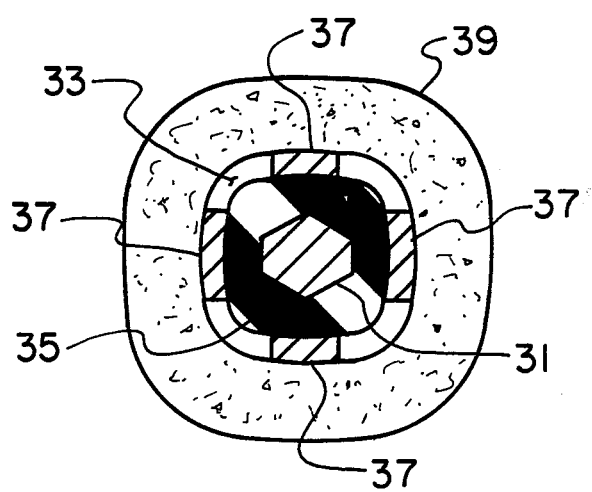
FIG. 4 is a cross-sectional view taken generally along the line 4—4 in FIG. 3.

Another embodiment of the present invention, labelled generally with the reference 29, is shown in FIGS. 3 and 4. In this embodiment, the flange portion 17 is attached to a stem 31 formed in the shape of the medullary canal 33 of the femur 39. A plurality of circumferential elastomeric rings 35 are attached to the stem 31 at spaced intervals along its length. Spacers 37, formed of porous titanium or a suitable equivalent, are attached at spaced intervals about each of the elastomeric rings 35 and extend radially outwardly into engagement with the cancellous and cortical bone in the medullary canal 33 of the femur 39. Four spacers 37 are used in the embodiment herein (see FIG. 4), but it is contemplated that as little as three spacers 37 could be utilized and more than four spacers 37 would also be suitable.

The solid stem 31 may be formed in several different configurations to minimize its bending stiffness while exhibiting sufficient strength to avoid failure under load. Stem 31 could be formed of a solid section of relatively stiff elastomer having a low spring rate, or if more stiffness is desirable, the elastomer could include a plurality of metal shims embedded at intervals along the length of stem 31. In the alternative, stem 31 may be split into two or more separate sections with elastomer attached therebetween as shown in the embodiments of FIGS. 2 and 2A. Depending on the spring rate characteristics of the elastomeric rings 35, the stem 31 could also be formed of solid titanium or an equivalent to obtain the proper bending stiffness of the prosthesis 29.

As in the embodiment of FIG. 1, the hip joint prosthesis 29 shown in FIG. 3 includes means to assure that the stem 31 remains in place within the medullary canal 33 of the femur 39 during the early stages of rehabilitation. The combined diameter of the stem 31, elastomeric rings 35 and spacers 37 is greater than that of the medullary canal 33, such that upon insertion of prosthesis 29 into the medullary canal 33 the elastomeric rings 35 are compressed and urge spacers 37 into contact with the femur 39. With the prosthesis 29 held relatively firmly in place within the femur 39 along its entire length, movement of the patient during the four to six weeks of postoperative bone and tissue ingrowth presents little danger of dislocating the prosthesis 29, unlike prior art devices.

Figure 5:
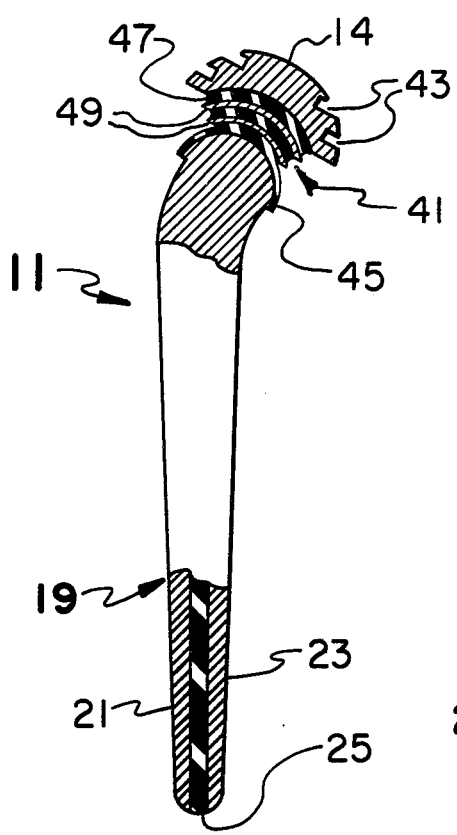
FIG. 5 is a perspective view in partial cross section showing the embodiment of FIG. 1 with the joint means of the present invention.
Figure 6:
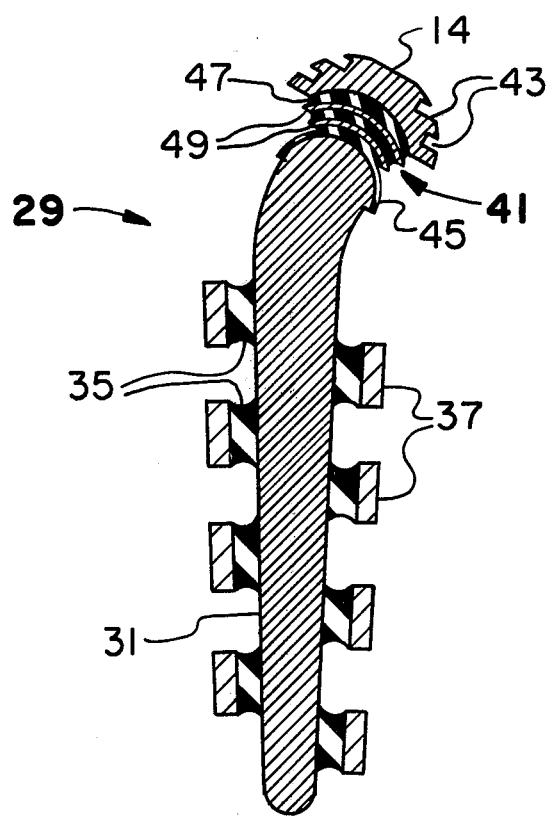
FIG. 6 is a perspective view in partial cross section showing the embodiment of FIG. 3 with the joint means of the present invention.

Referring now to FIGS. 5 and 6, the hip joint prostheses 11 and 29 of FIGS. 1 and 3, respectively, are shown in combination with joint means labelled generally with the reference 41. This combination eliminates the need for a separate acetabulum prosthesis, since the joint means 41 permits movement of the pelvis relative to the femur over the complete range of natural motion. The femoral head 14 is permanently secured to the acetabulum with bone cement or through bone ingrowth, and may be provided with annular grooves 43 for enhanced attachment in the event bone cement is utilized.

The joint means 41 consists of a generally spherical pivot component 45 attaching to the upper end of stem 19 (or stem 31 in FIG. 6), and a section of resilient elastomeric material 47 which is disposed between and attaches to pivot component 45 and femoral head 14. A plurality of curve shims 49 may be embedded at spaced intervals within elastomeric material 47 to increase the load carrying capability of the elastomeric material 47, resist bulging and simulate the soft tissue and ligament constraints found in a natural hip joint. The pivoting action of pivot component 45 permitted by the elastomeric material 47 provides prostheses 11 and 29 with three degrees of freedom of movement including movements of flexion and extension, abduction and adduction, and medial and lateral rotation. In addition, a relatively thin layer of elastomer may be provided on the outer surface of pivot component 45 to reduce stress concentrations which could occur at the interface between the pivot component 45 and the section of elastomeric material 47.

The present invention provides an improved hip joint prosthesis capable of significantly reducing bone resorption and necrotic degeneration often experienced after relatively short periods of time with prior art devices. In combination with joint means, the hip joint herein eliminates the need for a separate acetabulum prosthesis and provides a highly dependable alternative to the ball-and-socket type of joint action between the femoral head and acetabulum prostheses found in most prior art hip joints. It should also be noted that the problem of bone resorption and necrosis found in prior art complete hip joint prostheses can occur with an Austin Moore hemi arthroplasty and similar endoprostheses in which the femoral head is formed for contact with an undamaged acetabulum. The results of such partial hip joint replacement procedures can be improved by utilizing the stem configurations of the present invention (FIGS. 2, 2A and 3) in the Austin Moore and similar endoprostheses.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A joint prosthesis for replacement of the hip joint in a human body comprising:
    an acetabulum prosthesis formed in a hemispherical cup for attachment to the acetabulum cavity of the pelvis; and
    a femoral head prosthesis having a sphere at one end moveable within said cup of said acetabulum prosthesis, and having a stem at the other end shaped for insertion into the medullary canal of the femur, said stem being formed of at least one section of resilient elastomeric material disposed between and attaching to at least two spaced apart outer sections of rigid material, said section of resilient elastomeric material having at least a portion of its volume located as an innermost core part of said stem.

2. The joint prosthesis of claim 1 wherein said stem has a diameter greater than the diameter of said medullary canal of the femur such that upon insertion of said stem into said medullary canal said resilient elastomeric material is compressed and urges said sections of rigid material into contact with the femur for resisting movement of said prosthesis therewithin.

3. A joint prosthesis for replacement of the hip joint in a human body comprising:
    an acetabulum prosthesis formed in a hemispherical cup for attachment to the acetabulum; and
    a femoral head prosthesis having a sphere at one end moveable within said cup of said acetabulum prosthesis, and having a stem at the other end shaped for insertion into the medullary canal of the femur, said stem being formed of a layer of resilient elastomeric material disposed between and attaching to two spaced apart outer sections of rigid material, said layer of resilient elastomeric material having at least a portion of its volume located as an innermost core part of said stem.

4. A joint prosthesis for replacement of a hip joint in a human body comprising:
    an acetabulum prosthesis formed in a hemispherical cup for attachment to the acetabulum;
    a femoral head prosthesis having a sphere at one end moveable within said cup of said acetabulum prosthesis, and having a stem at the other end shaped for insertion into the medullary canal of the femur, said stem including a pair of layers of resilient elastomeric material oriented at a right angle to one another and disposed between and attaching to four spaced apart sections of rigid material.

5. A joint prosthesis for replacement of the hip joint in a human body comprising:
    an acetabulum prosthesis formed in a hemispherical cup for attachment to the acetabulum cavity of the pelvis; and
    a femoral head prosthesis having a sphere at one end moveable within said cup of said acetabulum prosthesis, said femoral head prosthesis having a stem at the other end shaped for insertion into the medullary canal of the femur, said stem including a core, a plurality of elastomeric rings attaching about the circumference of said core at spaced intervals along the length thereof, and a plurality of spacer means formed of rigid material attaching at spaced intervals to each of said elastomeric rings, said spacer means extending outwardly to contact the femur for supporting said prosthesis within the medullary canal.

6. The joint prosthesis of claim 5 wherein said core includes at least one layer of resilient elastomeric material disposed between and attaching to at least two spaced apart sections of rigid material.

7. The joint prosthesis of claim 5 wherein said core is a solid section or rigid material.

8. The joint prosthesis of claim 5 wherein said core is a section of essentially rigid elastomeric material having a plurality of metal shims embedded at spaced intervals therealong.

9. The joint prosthesis of claim 5 wherein said stem has a diameter greater than the diameter of said medullary canal of the femur such that upon insertion of said stem into said medullary canal said elastomeric rings are compressed and urge said spacer means into contact with the femur for resisting movement of said prosthesis therewithin.

10. The joint prosthesis of claim 5 wherein said spacer means are formed of a rigid biocompatible metal alloy having a surface porosity capable of accepting bone ingrowth.

11. A joint prosthesis for replacement of the hip joint in a human body comprising:

a head portion formed for attachment to the acetabulum of the pelvis;

a stem portion formed for insertion into the medullary canal of the femur, said stem including at least one section of resilient elastomeric material disposed between and attaching to at least two spaced apart sections of rigid material; and joint means including a pivot component formed at one end of said stem portion, and a body of elastomeric material disposed between and attaching to said pivot component and said head portion, said body of elastomeric material permitting three degrees of freedom of motion of said stem portion relative to said head portion in simulating the operating of a hip joint in the human body.

12. The joint prosthesis of claim 11 wherein said body of elastomeric material includes a plurality of shims embedded at spaced intervals therewithin.

13. A joint prosthesis for replacement of the hip joint in a human body comprising:

a generally spherical-shaped head portion formed for attachment to the acetabulum;

a stem portion shaped for insertion into the medullary canal of the femur, said stem including a section of resilient elastomeric material disposed between and attaching to two spaced apart sections of rigid material; and joint means including a pivot component formed at one end of said stem portion, and a body of elastomeric material disposed between and attaching to said pivot component and said head portion, said body of elastomeric material permitting three degrees of freedom of motion of said stem portion relative to said head portion in simulating the operation of a hip joint in the human body.

14. A joint prosthesis for replacement of the hip joint in a human body comprising:

a head portion formed for attachment to the acetabulum;

a stem portion shaped for insertion into the medullary canal of the femur, said stem including a core, a plurality of elastomeric rings attaching about the circumference of said core at spaced intervals along the length thereof, and a plurality of spacer means formed of a rigid material attaching at spaced intervals to each of said elastomeric rings, said spacer means extending outwardly to contact the femur; and joint means including a pivot component formed at one end of said stem portion, and a body of elastomeric material disposed between and attaching to said pivot component and said head portion, said body of elastomeric material permitting three degrees of freedom of motion of said stem portion relative to said head portion in simulating the operation of a hip joint in the human body.

15. A joint prosthesis for replacement of the hip joint in a human body comprising:

a generally spherical-shaped head portion for attachment to the acetabulum;

a stem portion shaped for insertion into the medullary canal of the femur, said stem including a pair of layers of resilient elastomeric material oriented at right angles to one another and disposed between and attaching to four spaced apart sections of rigid material; and joint means including a pivot component formed at one end of said stem portion, and a body of elastomeric material disposed between and attaching to said pivot component and said head portion, said body of elastomeric material permitting three degrees of freedom of motion of said stem portion relative to said head portion in simulating the operation of a hip joint in the human body.

* * * * *